United States Patent
McClain

(10) Patent No.: US 11,540,966 B2
(45) Date of Patent: Jan. 3, 2023

(54) GROSSING STATION CAMERA SYSTEM

(71) Applicant: MP Acquisition, LLC, Oak Park, MI (US)

(72) Inventor: Michael S. McClain, Waterford, MI (US)

(73) Assignee: MP ACQUISITION, LLC, Madison Heights, MI (US)

( * ) Notice: Subject to any disclaimer, the term of this patent is extended or adjusted under 35 U.S.C. 154(b) by 627 days.

(21) Appl. No.: 16/560,014

(22) Filed: Sep. 4, 2019

(65) Prior Publication Data
US 2020/0069497 A1 Mar. 5, 2020

Related U.S. Application Data

(60) Provisional application No. 62/727,285, filed on Sep. 5, 2018.

(51) Int. Cl.
| | | |
|---|---|---|
| *H04N 5/225* | (2006.01) | |
| *A61G 13/00* | (2006.01) | |
| *G06T 7/00* | (2017.01) | |
| *A61B 16/00* | (2006.01) | |

(52) U.S. Cl.
CPC .......... *A61G 13/0027* (2013.01); *A61B 16/00* (2013.01); *G06T 7/0012* (2013.01); *H04N 5/2252* (2013.01); *H04N 5/2256* (2013.01); *G06T 2207/10004* (2013.01)

(58) Field of Classification Search
CPC .. A61G 13/0027; A61B 16/00; G06T 7/0012; H04N 5/2252; H04N 5/2256
See application file for complete search history.

(56) References Cited

U.S. PATENT DOCUMENTS

| | | |
|---|---|---|
| 2,512,747 A | 6/1950 | Lewis |
| 2,702,505 A | 2/1955 | Nelson |
| 3,799,534 A | 3/1974 | Coles |
| 3,874,754 A | 4/1975 | Saunders et al. |
| 4,038,974 A | 8/1977 | Pielkenrood |
| 4,140,105 A | 2/1979 | Duvlis |
| 4,402,144 A | 9/1983 | Dumke |
| 4,422,369 A | 12/1983 | Smets |
| 4,650,171 A | 3/1987 | Haworth |
| 4,876,773 A | 10/1989 | Wade |
| 4,898,089 A | 2/1990 | Roos |
| 4,901,410 A | 2/1990 | Fischer et al. |
| 4,980,956 A | 1/1991 | Fischer et al. |
| 5,042,456 A | 8/1991 | Cote |
| 5,093,969 A | 3/1992 | McGuire |
| 5,181,883 A | 1/1993 | Hofstra et al. |
| 5,244,433 A | 9/1993 | Utterback |
| 5,303,659 A | 4/1994 | Berlin et al. |

(Continued)

FOREIGN PATENT DOCUMENTS

| | | |
|---|---|---|
| JP | 2003319943 | 11/2003 |
| WO | WO 2017141154 A1 | 8/2017 |

*Primary Examiner* — Jonathan R Messmore
(74) *Attorney, Agent, or Firm* — Raggio & Dinnin, P.C.

(57) ABSTRACT

A grossing station comprising a table and a hood connected to the table. The grossing station also comprises a quick release camera system secured to a surface of the hood, wherein the quick release camera system is detachable from the hood for close up angles and zoomed location still or video images of the body or material being examined on a surface of the grossing station.

19 Claims, 2 Drawing Sheets

(56) References Cited

U.S. PATENT DOCUMENTS

| | | | |
|---|---|---|---|
| 5,620,407 | A | 4/1997 | Change |
| 5,621,929 | A | 4/1997 | Smith |
| 5,904,162 | A | 5/1999 | Ferguson et al. |
| 6,050,660 | A | 4/2000 | Gurley |
| 6,279,510 | B1 | 8/2001 | Batterton |
| 6,503,163 | B1 * | 1/2003 | Van Sant ............. H04N 13/207 348/E13.016 |
| 6,694,892 | B2 | 2/2004 | Lin et al. |
| 7,428,882 | B2 | 9/2008 | Keil |
| 7,468,161 | B2 | 12/2008 | Reinhardt et al. |
| 9,463,129 | B2 | 10/2016 | Hallman |
| 10,194,876 | B1 * | 2/2019 | Gutkovich ............. A61B 6/504 |
| 2003/0033790 | A1 | 2/2003 | Hague |
| 2003/0130909 | A1 * | 7/2003 | Caci ................... G06Q 30/0641 705/26.81 |
| 2004/0016840 | A1 * | 1/2004 | Malvini ................. A45C 13/20 242/379.2 |
| 2005/0160948 | A1 | 7/2005 | Irwin |
| 2006/0154590 | A1 | 7/2006 | Kanaya |
| 2006/0180057 | A1 | 8/2006 | Hallman |
| 2008/0202491 | A1 | 8/2008 | Eberhard |
| 2012/0037049 | A1 | 2/2012 | Martin et al. |
| 2012/0260418 | A1 | 10/2012 | Rundberg et al. |
| 2015/0052975 | A1 | 2/2015 | Martin |
| 2015/0079894 | A1 | 3/2015 | Zimmerman |
| 2017/0087040 | A1 | 3/2017 | Hallman |
| 2017/0360639 | A1 | 12/2017 | Corona et al. |
| 2018/0055706 | A1 * | 3/2018 | Madadin ................... G06T 7/62 |
| 2019/0268574 | A1 * | 8/2019 | Tsukashima ....... A61B 17/0218 |
| 2019/0390858 | A1 * | 12/2019 | Chu ...................... F24C 15/006 |

* cited by examiner

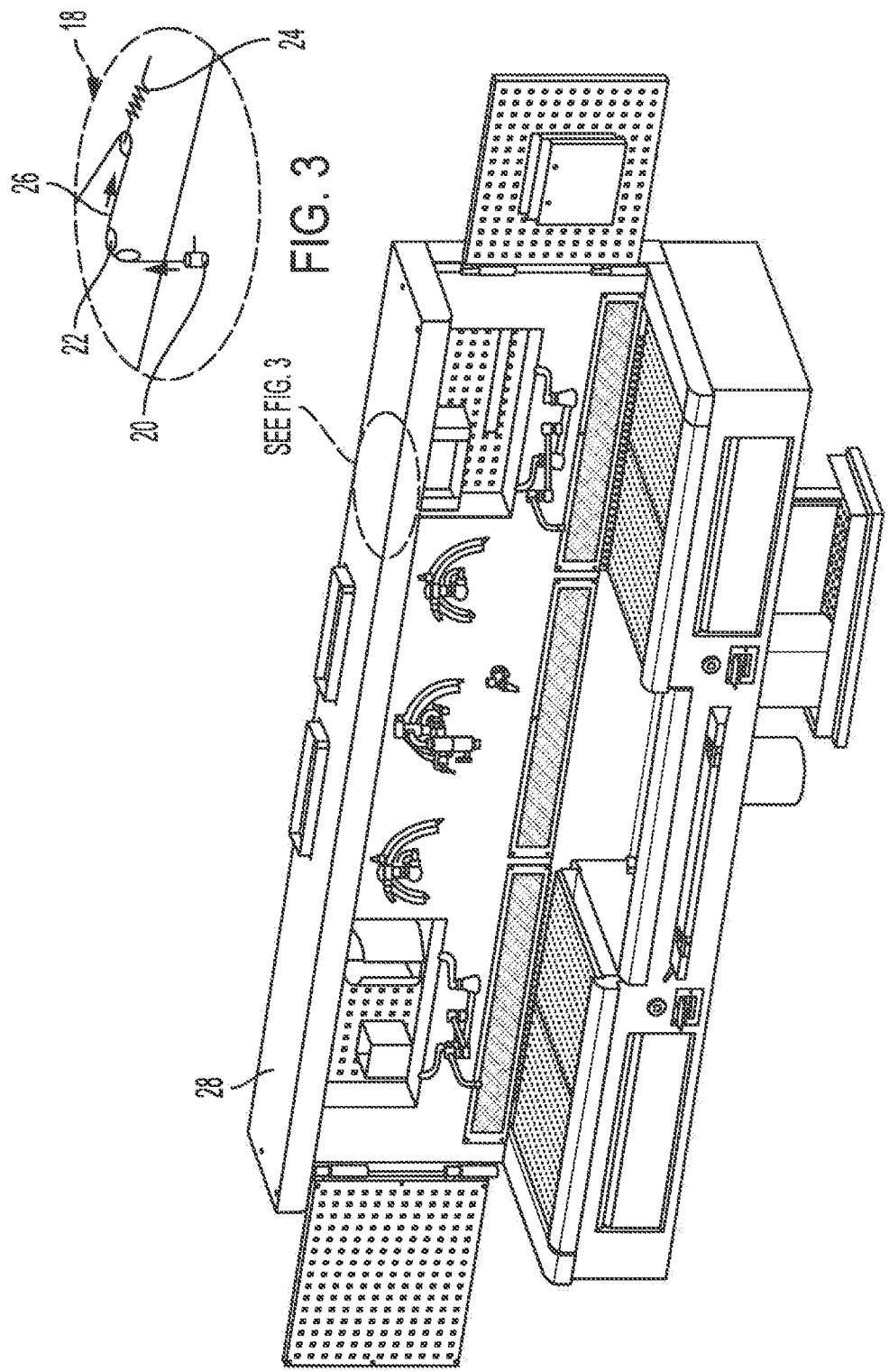

GROSSING STATION CAMERA SYSTEM

This application claims the benefit of U.S. Provisional Patent Application 62/727,285—Filed: Sep. 5, 2018

BACKGROUND OF THE INVENTION

1. Field of the Invention

The present invention generally relates to a grossing station or anatomy table and more particularly relates to a grossing station, anatomy table, or stands/lights having a quick release camera system.

2. Description of Related Art

Autopsy tables, grossing tables, necropsy tables, anatomy tables and trimming tables are all well known in the art. These tables are designed to accommodate a body or other part of a body while a post mortem examination is carried out, pathology is conducted on an organ or other body part or teaching of anatomy or other science is conducted thereon. Many of these autopsy tables and/or grossing stations in the prior art were made of simple ceramic slabs with no exhaust systems. Recently prior art autopsy tables have been made of a stainless steel having a discontinuous or perforated surface. These tables may have ventilation systems to reduce the odor associated with chemicals, natural fluids and components that are associated with an autopsy or pathology procedure. The use of ceramic slabs or stainless steel create an easy to clean surface that generally are non porous and easy to disinfect after each autopsy or pathology procedure is conducted.

Many of these prior art autopsy stations include an assortment of components used in conjunction therewith. For instance, an autopsy station may include a plurality of faucets that are used for transferring liquids, gas, or vapors to the autopsy station. Such liquids can be formaldehyde, other chemicals, water, or any other type of chemical or substance needed during an autopsy or pathology procedure. The autopsy tables of the prior art generally also include an air system that includes an air intake and air exhaust vents that may also include filters and the like to constantly clean the air and reduce odors from the autopsy table and surrounding environment. Furthermore, sinks are generally located within an autopsy table. Grating surfaces may also be located on the autopsy table for allowing fluids to be removed and collected during autopsy of the human or animal body. Furthermore, autopsy tables ray also be arranged such that a gurney or cart may be used in conjunction with the autopsy table or grossing station for delivering the body or for holding the body during the autopsy procedure. The gurney or cart may be capable of being secured in position against a predetermined surface of an autopsy table and may also be inclined to any required angle necessary for the user performing the autopsy. Prior art autopsy tables have generally been used in fixed positions in a post mortem room, hospital, laboratory or the like. Furthermore, these tables generally are fixed in a position that is convenient for a predetermined average size human to conduct the work of the autopsy or pathology procedures in a comfortable, non-stress inducing manner in a standing or seated position.

One possible problem associated with prior art autopsy, necropsy, grossing stations or tables is the ability to capture images of the material being autopsied on the grossing station. Another possible problem in the prior art is that cameras used for pictures during autopsy, necropsy, teaching, etc., have been fixed. So any videos or pictures have to be taken from a fixed angle, and the organ or body has to be moved to photograph a different spot or angle. The camera system of the present invention may allow the user to pull down the camera and aim it at the spot he/she wants photograph or video. It can also, of course, get closer than a fixed camera. A separate camera or other device has to be brought into the lab in order to take video images or still pictures of the material being autopsied in the prior art. There is no handheld integrated imaging capture system currently in use with a grossing station in the prior art. Therefore, there is a need in the art for an improved grossing station that has a quick release camera system incorporated therein. There also is a need in the art for a grossing station that is capable of having a quick release camera system that is easily detached from an interlocking mechanism in the hood or upwardly mounted system to be positioned by the hand of the person performing the autopsy at any usable angle about the work surface of the grossing station. There also is the need in the art for a grossing station that has an integrated quick release camera system that may include an integrated switch to allow capturing of still pictures, video recording and dictation to a recording system in communication to a storage system on the grossing station a network facility storage system or a cloud storage system.

SUMMARY OF THE INVENTION

One object of the present invention may be to provide a novel and unique grossing station.

Another object of the present invention may be to provide a grossing station that has an integrated quick release camera system arranged thereon.

Still another object of the present invention may be to provide a grossing station that has an integrated quick release camera system that is detachable from an interlock mechanism in the hood or an upwardly mounted system that may be positioned by hand of the user at any usable angle about the work surface of the grossing station.

Still another object of the present invention may be to provide a grossing station that has a quick release camera system that would automatically retract backup into the original location for stationary image capture from a predetermined position.

Yet another object of the present invention may be to provide a grossing station that has an integrated quick release camera system that may be integrated with a switch arranged on the grossing station to allow for capture of still pictures, video recordings, and dictation to a recording system which is in communication with a storage unit arranged on the grossing station, a network facility storage system or a cloud storage system.

According to the present invention, the foregoing and other objects and advantages are obtained by a novel design for a grossing station for use in an autopsy, necropsy or pathology procedure. The grossing station comprises a table and an overhead hood connected to the table. The grossing station may also comprise a blower and ventilation system arranged on the table. The grossing station may also comprise a plurality of interchangeable plates arranged in a trough to allow for either a left handed or right handed grossing station depending on the user of the grossing station. The grossing station may also comprise a lift system to allow for the height of the grossing station to be adjusted. The grossing station may also comprise a plurality of other systems arranged thereon. The grossing station may also comprise a quick release camera system that allows for the handheld use of an image capture device, such as a camera on the grossing station. The quick release camera system may include a camera that may detach from an interlocking mechanism arranged in the hood or that is upwardly mounted on some other surface in order to be positioned by the hand of the autopsy performer at any usable angle about the work surface. The detachable and removable camera may allow for close up user intuitive angles and zoomed in locations for still captured images and video images. The quick release camera system may be capable of retracting back up into its original location for stationary image capture and for storage when it is not being used. The quick release camera system may also be integrated with a switch arranged on a surface of the grossing station to allow for capture of still pictures, video recordings, and dictation to a recording system which is in communication with a storage unit arranged on the grossing station, a network facility storage system or a cloud storage system.

One advantage of the present invention may be that it provides a novel and unique grossing station.

Another advantage of the present invention may be that it provides for a grossing station having an integrated quick release camera system.

Still another advantage of the present invention may be to provide a grossing station that uses a quick release camera system that can detach from an interlock mechanism arranged in the hood or an upwardly mounted system of the grossing station and may be positioned by hand of the person performing the autopsy at any useable angle about the work surface of the grossing station.

Still another advantage of the present invention may be that it provides a grossing station with an integrated quick release camera system that would allow the camera to retract back up into its original or stored location in order to allow for stationary images to be taken by the camera at a predetermined position.

Yet another advantage of the present invention may be that it provides for a grossing station that uses a quick release camera system that may be integrated with a switch arranged on the grossing station to allow for capture of still pictures, video recordings and dictation to a recording system, which may be in communication with a storage unit on the grossing station, a network storage system or a cloud based storage system.

Other objects, features and advantages of the present invention will become apparent from the subsequent description, and appended claims taken in conjunction with the accompany drawings.

BRIEF DESCRIPTION OF THE DRAWINGS

FIG. 2 shows a perspective view of an autopsy sink with a quick release camera system according to the present invention.

FIG. 3 is a detailed view of circle 3 shown in FIG. 2 according to the present invention.

DESCRIPTION OF THE EMBODIMENTS

Figure 1:
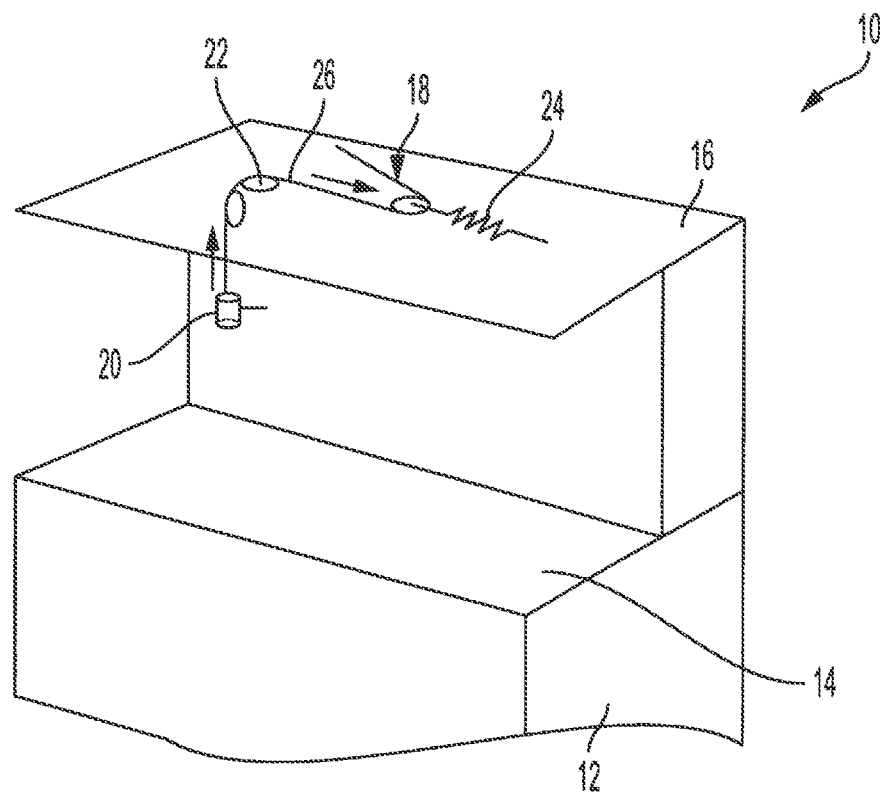
FIG. 1 show a perspective view of a grossing station with a quick release camera system according to the present invention.

Referring to the drawings, a grossing station 10 that is capable of being adjusted to various heights is shown according to the present invention. It should be noted that the grossing station 10 may be used on any known autopsy, necropsy, trimming, pathology, or any other procedure performed on tissues or the like all of which are for use in hospitals, morgues, funeral homes, university laboratories, other laboratories and any other structure that can be used for examining human or animal bodies or human and animal body parts.

The grossing station 10 of the present invention generally may include a base 12, which generally is arranged on a floor or other surface in a lab or room in which the grossing station 10 may be used. The base 12 may include a plurality of storage areas for storing formaldehyde or other materials needed during an autopsy. The grossing station 10 may also include a table or work surface area 14 arranged over a top portion of the base 12. The table 14 may have a generally rectangular and/or flat work surface arranged on a top end thereof. A lifting mechanism may be arranged between the base 12 and the table 14 of the grossing station 10. This may allow for the table 14 to be adjusted to any number of predetermined heights to accommodate different size users conducting the pathology procedures on the grossing station 10, It is also contemplated to use the table 14 without a base 12 and lifting mechanism. It should be noted that any type of lifting mechanism may be used on the grossing station 10 of the present invention, such as but not limited to a linear actuator, scissor actuator, screw actuator or any other lifting device, electronic, fluid driven, gas driven, air driven, electrical or mechanical driven, may be used to move the table 14 with relation to the base 12 to adjust the grossing station work surface to a predetermined height. It should be noted that a switch or switches may be arranged anywhere on the grossing station 10 for use in operating the height of the table, the blower and ventilation system, lights, computers, the quick release camera system, etc. The grossing station 10 may include a plurality of removable and interchangeable grid plates which may be arranged and fit securely into a trough of the table 14. The grid plates may allow for any combination or design of the table top of the grossing station 10 depending upon the user requirements.

The grossing station table 14 may also include a blower and ventilation system which may move air across the entire table including any sinks arranged within a top surface of the table in any known direction, such as a forward to rear direction, top to bottom direction, etc. The ventilation system may include any number of ventilation ducts and blowers arranged in any predetermined manner.

The grossing station 10 may also include a hood 16 that is secured to a top surface of the table 14 of the grossing station 10. The hood 16 generally may have two sidewalls and/or partial sidewalls, a rear wall and a top member. The top member when viewed from above, generally has a rectangular shape. The hood 16 may also include a flexible bellow duck, an access panel, a retention bracket and a back draft grill. It should be noted that any necessary lighting and associated electronics to control the lighting may be arranged on surfaces of the hood 16 or on the walls of the hood. The rear wall of the hood 16 may also include a plurality of shelves arranged thereon for holding supplies, tools, computer equipment, etc., or the lighting necessary for the pathology procedure being performed at the grossing station 10. The hood 16 may have a perforated back wall that allows for the placement of shelves, hooks or other components in a variety of configuration, depending on the user's requirements. The hood 16 is generally made of a stainless steel material as are all or most of the other parts and components of the grossing station 10, but may be made of any other metal, plastic, ceramic, composite, or natural material depending on the design requirements and the environment in which the grossing station 10 may be used.

In one contemplated embodiment, the use of sliding side glass panels may allow for the grossing station 10 to create a fume hood, which may be certified to remove all fumes from the autopsy, necropsy or pathology procedure, thus meeting more stringent standards required in some laboratories and hospital environments. It should be noted that all of the necessary piping, plumbing and electrical connections of the grossing station 10 are secured either to a surface of the hood 16, the table 14, or the base 12 of the grossing station 10 and are connected to the building systems in which the grossing station 10 is arranged. Copper tubing, rubber tubing, any necessary electronic circuitry, switches or any known pumps may be used to move the table 14 with relation to the base 12 and to move the air via the blower and ventilation system into either the outside atmosphere, storage area or a filter mechanism. Any known fasteners or holders, such as clips, rods, bands, screws, nuts, bolts, etc., may be used to secure the pipe, plumbing and electrical components to the surface of either the table 14, base 12, or hood 16 of the grossing station 10 according to the present invention. It is also contemplated to use the quick release camera system 18 according to the present invention on any other type of autopsy equipment, such as an autopsy sink 28 as shown in the drawings. As shown in the drawings, the autopsy sink 28 may also include perforated panels, a hood, a sink, faucets and other components arranged on or along the autopsy sink table/platform, the back wall and the hood.

The grossing station 10 of the present invention also may include a filter meter, an eco mode system, a remote warning system, an air flow monitoring system, an electronic control and monitoring system controller, a software controller system, an electrical system that uses a touch screen controller, an improved lighting system, a formalin refill system, and an integrated gas sensor system arranged on the grossing station 10 in some manner. It should be noted that some or all of these components may be on the grossing station 10 or none of these components may be arranged on the grossing station 10, depending on the specific requirements of the environment in which the grossing station 10 may be used.

The grossing station 10 of the present invention may also include an integrated quick release camera system 18 that may allow for handheld use of an image capture system, such as a camera 20, on the grossing station 10. The quick release camera system 18 generally may include any type of camera 20, a plurality of pulleys 22, a spring 24, and a self retracting cable 26, such as any known metal cable, plastic cable, ceramic cable, composite cable, or natural material cable. It should be noted that any type of handheld camera 20 may be used with the quick release camera system 18 according to the present invention. In one contemplated embodiment, a small digital camera may be used. The camera 20 may be capable of capturing still images and recording video. It is contemplated that the camera may be capable of zooming and recording with or without sound hence it may include a capable microphone and speaker arranged thereon to allow for playback to the user of the quick release camera system 18 on the grossing station 10.

The quick release camera system 18 may also include at least one pulley 22 and a spring 24 arranged within or on a surface/component the hood 15 of the grossing station 10. It should be noted that any other number including zero pulleys 22 or springs 24 may also be used. The spring 24 and pulleys 22 may allow for the camera 20 to be self retracting wherein the cable 24 is wound around the pulleys 22. The spring 24 may be attached to one of the pulleys 22 and a surface of the hood 15 to allow for a predetermined spring coefficient and force to be applied to the system to allow for the precise control needed when the user removes the camera 20 from its storage position to a predetermined position for up close pictures or videos of the material being autopsied. It should be noted that the camera 20 may have an interlock mechanism that may allow for it to be locked in position on or in the hood 16 and then removed easily from the hood 16 via either a tab/switch, a quick release button or a rotating mechanism that may allow for the camera 20 to be removed from its secured storage location on the hood 16 via a predetermined rotation or movement of the camera 20 or switch/button, with relation to a surface of the hood 16. Therefore, the camera 20 being easily detachable from an interlock mechanism of the hood 16 or other upwardly mounted system, may allow for the camera 20 to be pulled down to a specific location of the work surface of the grossing station 10 by the hand of the person performing the autopsy. The camera 20 may than be held by the user thereof at any usable angle. This may allow for close up user intuitive angles and zoomed in locations for both still and video images on the material being autopsied. When the user of the camera 20 has finished taken their still images or videos, the quick release camera system 18 may allow for the camera 20 to be retracted automatically back up into its original or stored location within the bottom surface of the hood 16 of the grossing station 10. When in its original location, the camera 20 may be capable of taking pictures from a fixed stationary point, thus allowing for other views of the material being autopsied. It is also contemplated that the quick release camera system 18 of the present invention may be integrated or electrically connected with a switch that may allow for the capturing of videos and still images via the push of a button or switch arranged anywhere on the work surface or other surface of the autopsy table 14, base 12 or hood 16 or at a remote location such as with a key fob. This may allow for the user to hold the camera 20 at a predetermined position with one hand and then hit a button or switch on the grossing station 10 to either capture a still image or record a video of the material being autopsied. It is also contemplated that when the camera 20 is in its storage location or original location, that the user of the autopsy table may press a switch either on the grossing station 10 or on the camera 20 directly to take pictures/videos or audio from a stationary point of view. It should be noted that the camera 20 may be operated by directly pressing a button arranged directly on the camera 20, by pressing a button arranged on the grossing station 10 that may electronically operate the camera 20 to take the necessary images. It is also contemplated that the quick release camera system 18 may include a dictation system that may allow for the recording of words used in association with the pictures taken by the person performing the autopsy. This may allow for a complete image and audio record to be created for the autopsy being performed thereon. It should be noted that both the camera and associated dictation system that either may be incorporated into the camera or incorporated directly into another portion of the grossing station 10, may both be in communication with a storage unit arranged either directly on or within the grossing station 10, in communication with a network facility storage system or in communication with a cloud storage system. This may allow for many different methods of storing the material captured by the camera both video and audio to a recording system for future use by the person performing the autopsy.

It should be noted that any type of reel, pulley 22 and spring system, or other storage system/methodology may be used to retract the cable 26 of the quick release camera system 18 according to the present invention. The ability to automatically self retract the cable after use of the camera 20 by the user of the grossing station 10 has not been shown in the prior art. It is also contemplated that the camera 20 may be attached or detached from an end of cable 26 by any known fastener. The camera 20 may also be detached from cable 26 during the capture of images therewith. It should further be noted that any type of ratchet system may also be incorporated therein, wherein pulling down of the camera 20 may latch or lock the cable 26 at a predetermined position until the camera 20 or cable 26 is pulled/released and thus retracted via a coil spring or any other type of mechanism to its reel or other storage location. Generally, a reel is the preferred method for storing the excess cable that is used to allow for the camera 20 to be moved to various locations anywhere on the work surface of the grossing station 10. It should be noted that any type of fasteners may be used to secure the pulleys 22 and springs 24 used in the quick release camera system 18 to the hood 16. It should be noted that any other type of system that is capable of being easily detachable from the hood 16 may be connected to the camera 20 to allow for the camera 20 to be easily moved and then retracted back in to its original location after use by the autopsy performer. It is also contemplated to have a light arranged directly on the camera 20 to allow for images to be captured with a flash or light arranged directly on or near the camera 20 to allow for better visual images of the material being autopsied. It should be noted that when the invention is not used with a grossing station 10, the camera 20 may typically be mounted on a light, but it may be mounted on a stand with or without a light. Hence, while some of the quick release camera systems 18 may generally be housed on or with grossing stations 10, it is also contemplated to use the quick release camera system 18 by attaching it to a light or a stand. This may allow it to be used with an anatomy table or an autopsy table, but it may or may not be affixed to the table 14.

The present description is for illustrative purposes only and it should not be construed to limit the present invention in any way. Thus, a person skilled in the art will appreciate that various modifications might be made to the present and disclosed embodiments without departing from the scope and spirit of the present invention, which is defined in terms of the claims below. Other aspects, features, and advantages may be apparent upon an examination of the attached drawing figures and appended claims.

What is claimed is:

1. A grossing station, said grossing station comprising:
a table;
a hood connected to said table; and
a quick release camera system secured to a bottom surface of said hood, said quick release camera system is detachable from said hood for close up angle or zoomed still or video images, said quick release camera system having at least one pulley arranged on or in said hood, said quick release camera system having a self retracting cable removably connected to said camera on one end of said self retracting cable.

2. The grossing station of claim 1 comprising an autopsy sink arranged in said table.

3. The grossing station of claim 1 wherein said quick release camera system having a handheld camera for capturing said still or video images.

4. The grossing station of claim 3 wherein said camera captures pictures from a fixed stationary point when in a stored position on said bottom surface of said hood.

5. The grossing station of claim 1 wherein said quick release camera system having a spring arranged between said pulley and a surface of said hood.

6. The grossing station of claim 1 wherein at least one pulley having a plurality of pulleys arranged on or within said hood.

7. The grossing station of claim 1 wherein said self retracting cable having a ratchet system.

8. The grossing station of claim 1 wherein said self retracting cable automatically moves said camera back to a stored location after said images are taken.

9. The grossing station of claim 1 wherein said quick release camera system having an interlock mechanism which removably secures a camera to said hood.

10. The grossing station of claim 9 wherein said interlock mechanism having a tab, switch or button to release said camera from said hood.

11. The grossing station of claim 3 wherein said camera captures images by using a button or switch on a surface of said hood or said table.

12. The grossing station of claim 1 wherein said captured images are stored on said camera or an off camera storage system.

13. The grossing station of claim 3 wherein said camera having a light arranged thereon, said camera captures images using a button or switch on said camera.

14. The grossing station of claim 1 wherein said quick release camera system is mounted on a stand, said stand is secured to said hood or table.

15. A quick release camera system for use on a grossing station, said system comprising:
a handheld camera arranged on a bottom surface of a hood of the grossing station;
an automatically self retracting cable connected to said camera;
at least one pulley having said self retracting cable arranged thereon;
a spring connected to said at least one pulley; and
said handheld camera is removably secured to said surface of the grossing station for capturing still or video images.

16. The system of claim 15 wherein the grossing station is an autopsy sink.

17. The system of claim 15 wherein said self retracting cable having a ratchet system.

18. The system of claim 15 wherein said camera having an audio recording device and a light.

19. The system of claim 15 wherein said camera captures said images via a button on said camera or a button arranged on a surface of the grossing station.

* * * * *